United States Patent [19]
Tessier-Lavigne et al.

[11] Patent Number: 6,096,866
[45] Date of Patent: Aug. 1, 2000

[54] NETRINS

[75] Inventors: Marc Tessier-Lavigne, San Mateo; Tito Serafini; Timothy Kennedy, both of San Francisco, all of Calif.; Marysia Placzek, London, United Kingdom; Thomas Jessell, New York, N.Y.; Jane Dodd, New York, N.Y.

[73] Assignees: The Regents of the University of California, Oakland, Calif.; Columbia University, New York, N.Y.

[21] Appl. No.: 08/650,599

[22] Filed: Jun. 7, 1995

Related U.S. Application Data

[62] Division of application No. 08/152,019, Nov. 12, 1993, Pat. No. 5,565,331.

[51] Int. Cl.[7] .............................. C07K 7/00; C07K 14/475
[52] U.S. Cl. ......................... 530/350; 530/324; 530/325; 530/326; 530/327; 530/328; 530/329
[58] Field of Search ...................................... 530/300, 350, 530/399, 324–330; 514/2, 12–18; 435/325

[56] References Cited

U.S. PATENT DOCUMENTS 5,565,331  10/1996  Tessier-Lavgne .

OTHER PUBLICATIONS

Yee et al., Neuran, 24:607–622, Nov. 1999.
Hopker et al., Nature, 401:69–73, Sep. 1999.
Bloch–Gallego et al., *Journal of Neuroscience*, 19(11):4407–4420, Jun. 1999.
Galko et al, *Society for Nerroscience Abstracts* Nov. 1994 vol. 20 p. 297 (item 533.19).
Harlowe and Lane "Antibodies A Laboratory Manual"(1988) Cold Spring Harbour Laboratory, USA p. 76.
Durkin et al. *Biochemistry* (1988) vol. 27 pp. 5198–5204.
Sasaki et al *JBC* (1987) vol. 262 No. 35 pp. 17111–17117.
Ogawa et al *JBC* (1988) vol. 263 No. 17 pp. 8384–8389.
Barlow et al. *EMBO J* (1984) vol. 3 No. 10 pp. 2355–2362.
Serafini et al *Cell* (1994) vol. 78 pp. 409–424.
Kennedy et al *Cell* (1994) vol. 78 pp. 425–435.

*Primary Examiner*—Marianne P. Allen
*Attorney, Agent, or Firm*—Richard Aron Osman

[57] ABSTRACT

Netrins, nucleic acids which encode netrin proteins and hybridization reagents, probes and primers capable of hybridizing with netrin genes and methods for screening chemical libraries for lead compounds for pharmacological agents are provided.

13 Claims, No Drawings

NETRINS

RELATED APPLICATION

This application is a divisional in part of Ser. No. 08/152,019 filed Nov. 12, 1993, issued as U.S. Pat. No. 5,565,331 directed to the invention of the non-elected Group I.

The research carried out in the subject application was supported in part by grants from the National Institutes of Health. The government may have rights in any patent issuing on this application.

INTRODUCTION

1. Field of the Invention

The field of this invention is vertebrate netrin proteins and genes which are involved in neural axon outgrowth.

2. Background

In the developing nervous system, axons project considerable distances along stereotyped pathways to reach their targets. Axon growth and guidance depends partly on the recognition of cell-surface and extracellular matrix cues along these pathways. The identification of such nerve cell growth and guidance cues is the holy grail of neurobiology. These are the compounds that tell neurons when to grow, where to grow, and when to stop growing. The medical applications of such compounds are enormous and include modulating neuronal growth regenerative capacity, treating neurodegenerative disease, and mapping (e.g. diagnosing) genetic neurological defects.

Over decades of concentrated research, various hypotheses involving chemo-attractants and repellents, labeled pathways, cell adhesion molecules, etc. have been invoked to explain guidance. Molecules such as N-CAM and N-cadherin have been reported to provide favorable substrates for axon growth and certain sensory axons may be responsive to NGF and NGF-like factors. Recent reports suggest the existence of diffusible chemotropic molecule(s) which influence the pattern and orientation of commissural axon growth.

Relevant Literature

Placzek et al. (1990) Development 110, 19–30; Placzek et al. (1990) Cold Spring Harbor Symposia on Quantitative Biology 55, 279–302.; and Tessier-Lavigne et al. (1988) Nature 336: 775–778 report evidence for diffusible chemotropic molecules which influence the pattern and orientation of commissural axon growth. Gundersen and Barret (1980) JCB 87, 546–554, Lohof et al. (1992) J. Neurosci. 12 (4), 1253–1261 and Zheng et al. (1993) Soc. Neurosci. Abstr 19, 608.9 report neural chemotaxis in response to NGF, cAMP and acetylcholine, respectively. Ishii et al. (1992) Neuron 9, 873–881 disclose a gene, unc-6, derived from C. elegans, which has sequence similarity to the disclosed netrins. Data disclosed in this application was published in Serafini et al (1994) Cell 78, 409–424 and Kennedy et al (1994) Cell 78, 425–435 at page 5, column 1. The work was also reported in *The New York Times*, Section B7, Tuesday, Aug. 16, 1994 and more recently (May 19, 1995) described in Science 268, 971–973 (see also references cited therein).

SUMMARY OF THE INVENTION

The invention provides methods and compositions relating to netrins and netrin genes. Netrins are a novel class of proteins which are naturally involved in neural axon guidance. The subject compositions include nucleic acids which encode netrin proteins and hybridization probes and primers capable of hybridizing with netrin genes. Netrins find particular use in modulating neural axon outgrowth. The disclosed compositions also find use variously in screening chemical libraries for regulators of axon outgrowth and orientation, in genetic mapping, as probes for related genes, as diagnostic reagents for genetic neurological disease and in the production of specific cellular and animal systems for the development of neurological disease therapy.

DETAILED DESCRIPTION OF THE INVENTION

The invention provides methods and compositions relating to netrins and netrin genes; including methods and compositions for identifying, purifying, characterizing, and producing netrins and for identifying, characterizing, cloning, expressing, inhibiting the expression of and amplifying netrin genes.

Netrins are characterized by sequence similarity to the disclosed netrins 1 and 2. Using the amino acid sequence search program BLASTP (Altschul et al. (1990) Basic Local Alignment Search Tool, J Mol Biol 215, 403–410), complete (full length) netrin amino acid sequences provide a Probability P(N) score of less than $1.0e{\cdot}200$. In contrast, complete amino acid sequence comparison of a netrin with the evolutionary related laminin proteins provides P(N) scores exceeding $1.0e{\cdot}144$. In addition, netrins generally show at least about 25% overall pair-wise sequence identity with all of the disclosed netrins 1 and 2 and at least about 50% pair-wise sequence identity within domain V. Furthermore, netrins are generally characterized by netrin-specific amino acid sequences invariant across the disclosed netrins 1 and 2, as seen in their amino acid alignments. The subject netrins may be incomplete translates of the disclosed netrin cDNA sequences or deletion mutants of the corresponding conceptual translates, which translates or deletion mutants have the netrin binding activity and specificity described herein.

The claimed netrins are isolated, partially pure or pure and are typically recombinantly produced. An "isolated" protein for example, is unaccompanied by at least some of the material with which it is associated in its natural state and constitutes at least about 0.5%, preferably at least about 2%, and more preferably at least about 5% by weight of the total protein in a given sample; a partially pure protein constitutes at least about 10%, preferably at least about 30%, and more preferably at least about 60% by weight of the total protein in a given sample; and a pure protein constitutes at least about 70%, preferably at least about 90%, and more preferably at least about 95% by weight of the total protein in a given sample. A wide variety of molecular and biochemical methods are available for generating and expressing the subject compositions, see e.g. Molecular Cloning, A Laboratory Manual (Sambrook, et al. Cold Spring Harbor Laboratory), Current Protocols in Molecular Biology (Eds. Aufubel, et al., Greene Publ. Assoc., Wiley-Interscience, NY) or that are otherwise known in the art.

The disclosed netrin compositions may be used to modulate axon outgrowth or guidance in situ or in vivo. For in vivo applications, the compositions are added to a retained physiological fluid such as blood or synovial fluid. For CNS administration, a variety of techniques are available for promoting transfer of the therapeutic across the blood brain barrier including disruption by surgery or injection, drugs which transiently open adhesion contact between CNS vasculature endothelial cells, and compounds which facilitate translocation through such cells. Netrins may also be amenable to direct injection or infusion, topical, intratracheal/nasal administration e.g. through aerosol, intraocularly, or within/on implants e.g. fibers e.g. collagen, osmotic pumps, grafts comprising appropriately transformed cells, etc. A particular method of administration involves coating, imbedding or derivatizing fibers, such as collagen fibers, protein polymers, etc. with therapeutic proteins. Other useful approaches are described in Otto et al. (1989) J Neuroscience Research 22, 83–91 and Otto and Unsicker (1990) J Neuroscience 10, 1912–1921. Generally, the amount administered will be empirically determined, typically in the range of about 10 to 1000 µg/kg of the recipient and the concentration will generally be in the range of about 50 to 500 µg/ml in the dose administered. Other additives may be included, such as stabilizers, bactericides, etc. will be present in conventional amounts.

The invention provides netrin-specific binding agents including isolated binding targets such as membrane-bound netrin receptors and netrin-specific antibodies and binding agents identified in screens of natural and synthetic chemical libraries, and methods of identifying and making such agents, and their use in diagnosis, therapy and pharmaceutical development. Generally, netrin-specificity of the binding agent is shown by binding equilibrium constants. Such agents are capable of selectively binding a netrin, i.e. with an equilibrium constant at least about $10^7 M^{-1}$, preferably at least about $10^8 M^{-1}$, more preferably at least about $10^9 M^{-1}$. A wide variety of cell-based and cell-free assays may be used to demonstrate netrin-specific binding; preferred are rapid in vitro, cell-free assays such as mediating or inhibiting netrin-cell/protein binding, immunoassays, etc.

The invention also provides nucleic acids encoding the subject proteins, which nucleic acids may be part of netrin-expression vectors and may be incorporated into recombinant cells for expression and screening, transgenic animals for functional studies (e.g. the efficacy of candidate drugs for neural disease or injury), etc. and nucleic acid hybridization probes and replication/amplification primers having a netrin cDNA specific sequence. The hybridization probes contain a sequence common or complementary to the corresponding netrin gene sufficient to make the probe capable of specifically hybridizing to the corresponding netrin gene in the presence of laminin genes. Hybridization probes having in excess of 100 continuous bases of netrin gene sequence are generally capable of hybridizing to the corresponding netrin cDNA and remaining bound at a reduced final wash stringency of 0.2×SSC (0.9M saline/0.09M sodium citrate) and 0.1% SDS buffer at a temperature of 65° C.

Netrin genes, the term including natural genomic and mRNA/cDNA sequences, are characterized by sequence similarity to the disclosed netrin 1 and 2 cDNAs. Using the nucleic acid sequence search program BLASTX (Altschul et al. (1990) Basic Local Alignment Search Tool, J Mol Biol 215, 403–410), complete coding region (full length) netrin cDNA sequences provide a Probability P(N) score of less than 1.0e-200. In contrast, complete coding region nucleic acid sequence comparison of a netrin cDNA with the evolutionary related laminin cDNAs provides P(N) scores exceeding 1.0e-144. In addition, netrin cDNAs generally show at least about 25% overall coding region pair-wise sequence identity with the disclosed netrins 1 and 2 cDNAs and at least about 35% domain V coding region pair-wise sequence identity. Furthermore, netrin genes are generally characterized by netrin gene-specific nucleic acid sequences invariant across the disclosed netrin 1 and 2 cDNAs, as seen in their nucleic acid alignments. Vertebrate netrin genes derive from vertebrates.

The subject nucleic acids are isolated, meaning they comprise a sequence joined to a nucleotide other than that which it is joined to on a natural chromosome and usually constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction. The subject nucleic acids find a wide variety of applications including use as translatable transcripts, hybridization probes, PCR primers, therapeutic nucleic acids, etc.; use in detecting the presence of netrin genes and gene transcripts, in detecting or amplifying nucleic acids encoding other netrins, and in gene therapy applications, e.g. antisense oligonucleotides capable of inhibiting the intracellular expression of a targeted netrin transcript.

The invention provides efficient methods of identifying pharmacological agents or lead compounds for agents capable of mimicking or modulating netrin function (e.g. bioactive netrin deletion mutants and netrin peptides). A wide variety of screens may be used; for example, cell-based assays for may be used for monitoring netrin function and in vitro binding assays may be used to identify netrin-specific binding agents. Kennedy Tessier-Lavigne et al. (1988, supra) describe an essay for netrin activity and (1994) Cell 78, 425–435 describe a particularly convenient COS cell-based netrin expression assay. Preferred methods are amenable to automated, cost-effective high throughput screening of natural and synthetic chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

NETRIN GENE CLONING STRATEGIES

Vertebrate netrin genes are cloned using the using the two general cloning strategies illustrated below for mouse and human netrins. First, using a strategy based on the initial amplification of a PCR product, oligonucleotide primers are designed using amino acid and nucleic acid sequences conserved among the previously identified vertebrate netrin sequences. Using these primers, a partial cDNA clone, corresponding to the novel netrin of interest is amplified from cDNA ergonomic DNA from the tissue and organism of interest by PCR. This partial clone is then used to generate a labeled probe which is used to screen a cDNA library or genomic library at high stringency to isolate a full length cDNA corresponding to the clone of interest. We describe below how such a strategy, based on PCR followed by library screening, has been used to successfully isolate mouse netrin-1,Drosophila netrin-a, and two human netrin cDNAs. The second general strategy utilizes reduced stringency library screening (Sambrook et al., 1989). We demonstrate below the applicability of this method in the isolation of mouse netrin-2. In this case we amplified and incorporated 80P into a probe which corresponded to domains VI and V in chicken netrin-2. Domains VI and V contain a number of regions of sequence which are well conserved among all vertebrate netrin family members isolated to this date. This probe was then used to screen an embryonic mouse brain cDNA library at reduced stringency. Our cloning of mouse netrin-2 using this method demonstrates that hybridization conditions are conveniently established which will detect netrin sequences between vertebrate species while avoiding significant background hybridization to non-netrin clones.

Our data identify netrin sequences common to the vertebrate netrins, mouse netrin-1, chicken netrin-1, and chicken netrin-2, which are not shared by the invertebrate netrin unc-6 as seen in netrin sequence alignments. The presence of these sequences, specific to vertebrates and conserved in all vertebrate netrins isolated, provides the necessary and sufficient sequence informative for generating primers and/or probes for any vertebrate netrin gene. In addition, amino acid sequence alignments similarly demonstrate that the vertebrate netrins define a structural class sharing common sequences not shared with the invertebrate species illustrated by C. elegans unc-6 and the Drosophila Melanogaster netrin-a. Furthermore the alignment between the Drosophila and the C, elegans sequences indicates there is a greater diversity of netrin amino acid sequence represented within the invertebrate phylum than is present within the sequences derived from the vertebrate phylum.

The following examples are offered by way of illustration and not by way of limitation.

EXAMPLES

We isolated chicken netrin 1 and 2 cDNAs as described in Sarafini et al. (1974) *Cell* 78:409–424. Based on the ckick netrin 1 and 2 cDNA sequences, we designed degenerate oligonucleotide primers and used these primers to amplify a cDNA encoding mouse netrin 1 from a murine cDNA library.

We isolated a mouse netrin-2 cDNA from a screen of a P0 (day of birth) mouse brain cDNA library (stratagene 937319: mouse P0 brain cDNA library in ZAPXP, oriented cloning). The probe used corresponded to sequences within domains VI and V of chicken netrin-2. Domain VI and V of the netrins contain regions of nucleic acid and amino acid sequence highly conserved in all netrins in each of the vertebrate species characterized to this date. The probe was labeled by incorporation of 82P during PCR using a template of chicken netrin-2 cDNA.

$1 \times 10^6$ clones were screened at a reduced final wash stringency of 0.2×SSC and 0.1% SDS at 65 A1C (Sambrook et al., 1989). A single ~7.5 kb clone corresponding to mouse netrin-2 CDNA was obtained. Sequencing of this CDNA indicated that it comprises over 40% of the netrin coding sequence but is lacking sequence corresponding to the 5' coding sequence of mouse netrin-2. To isolate the 5' coding sequence from cDNA isolated from CDNA libraries, we have employed a combination of library screening and PCR using standard methods (Sambrook et al., 1989).

We first isolated a human netrin cDNA using the degenerate oligonucleotide primers. The primers were constructed using amino acid sequences conserved in the previously isolated chick and mouse netrin sequences as a guide. The starting material for PCR was 100 ng of human genomic DNA.

PCR products were subcloned and individual clones containing inserts corresponding to human netrin sequence isolated using a Grunstein and Hogness screen (Sambrook, 1989). 82P was incorporated into a probe using PCR with a portion of the mouse netrin-1 cDNA clone as a template. The final wash of the filters was at a reduced stringency of 1×SSC and 0.1% SDS at 65° C. (Sambrook et al., 1989). This screen isolated an approximately 140 base pair human netrin cDNA clone. This cDNA fragment was used to isolate a longer human netrin cDNA from a Human fetal brain cDNA library (Stratagene cat #936206). The ~140 base pair human netrin cDNA was used as a template and 32P incorporated into a human netrin cDNA probe using PCR. $1 \times 10^6$ clones were screened at high stringency (Sambrook et al., 1989) identifying a single approximately 7 kb netrin cDNA. Sequence obtaining from the ends of this clone encode untranslated DNA sequence (see tables 9 and 10), indicating a full length clone. Internal sequence of the cDNA obtained using oligonucleotide primers corresponding to sequences contained in the ~140 clone, confirm and extend that sequence in the larger clone. Searches of the NBRF amino acid and nucleic acid sequence databases indicate that the published sequences with which this human cDNA shares the highest sequence identity are those of chicken netrin-1 and chicken netrin-2, the only vertebrate netrin sequences contained in the database at this date. In addition, these sequences encode amino acid sequences indicating that this clone represents a human netrin cDNA.

A partial cDNA was first amplified by PCR using non-degenerate primers designed using the codon usage for Drosophila as a guide. The particular sequences used were chosen on the basis of their conservation in the amino acid sequences of the invertebrate netrin gene unc-6 and the chicken netrin-1 and netrin-2 cDNAs. Nested PCR amplification was performed using 1 ng of total embryonic Drosophila cDNA as a template. A full length cDNA corresponding to Drosophila melanogaster netrin-a was then isolated by screening a cDNA library at high stringency using standard methods (Sambrook et al., 1989).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated polypeptide comprising a vertebrate netrin or portion thereof which modulates axon outgrowth or guidance or elicits a vertebrate netrin-specific antibody, wherein said vertebrate netrin is selected from the group consisting of a chicken netrin-1 (SEQ ID NO:01) and a chicken netrin-2 (SEQ ID NO:02).

2. The polypeptide of claim 1 comprising an amino acid sequence selected from the group consisting of: SEQ ID NO:01, residues 289–294; SEQ ID NO:02, residues 265–270; SEQ ID NO:01, residues 296–304; SEQ ID NO:02, residues 272–280; SEQ ID NO:01, residues 308–315; SEQ ID NO:02, residues 284–291; SEQ ID NO:01, residues 320–338; SEQ ID NO:02, residues 296–319; SEQ ID NO:01, residues 345–350; SEQ ID NO:01, residues 352–368; SEQ ID NO:02, residues 328–344; SEQ ID NO:01, residues 373–380; SEQ ID NO:02, residues 349–356; SEQ ID NO:01, residues 385–401; SEQ ID NO:02, residues 361–377; SEQ ID NO:01, residues 408–416; SEQ ID NO:02, residues 384–392; SEQ ID NO:01, residues 418–423; SEQ ID NO:02, residues 394–399; SEQ ID NO:01, residues 427–434; SEQ ID NO:02, residues 403–410; SEQ ID NO:01, residues 439–451; SEQ ID NO:02, residues 415–427; SEQ ID NO:01, residues 453–459; SEQ ID NO:02, residues 429–435; SEQ ID NO:01, residues 466–478; SEQ ID NO:02, residues 442–454; SEQ ID NO:01, residues 485–499; SEQ ID NO:02, residues 461–475; SEQ ID NO:01, residues 513–523; SEQ ID NO:02, residues 489–499; SEQ ID NO:01, residues 545–550; SEQ ID NO:02, residues 521–526; SEQ ID NO:01, residues 573–584; SEQ ID NO:02, residues 549–560; SEQ ID NO:01, residues 528–537; SEQ ID NO:02, residues 504–513; SEQ ID NO:01, residues 40–45; SEQ ID NO:02, residues 27–30; SEQ ID NO:01, residues 51–65; SEQ ID NO:02, residues 38–52; SEQ ID NO:01, residues 68–75; SEQ ID NO:02, residues 55–62; SEQ ID NO:01, residues 97–107; SEQ ID NO:01, residues 109–116; SEQ ID NO:02, residues 80–87; SEQ ID NO:01, residues 117–123; and SEQ ID NO:02, residues 88–94.

3. The polypeptide of claim 1 comprising an amino acid sequence selected from the group consisting of: SEQ ID NO:01, residues 289–294; SEQ ID NO:01, residues 296–304; SEQ ID NO:01, residues 308–315; SEQ ID NO:01, residues 320–338; SEQ ID NO:01, residues 345–350; SEQ ID NO:01, residues 352–368; SEQ ID NO:01, residues 373–380; SEQ ID NO:01, residues 385–401; SEQ ID NO:01, residues 408–416; SEQ ID NO:01, residues 418–423; SEQ ID NO:01, residues 427–434; SEQ ID NO:01, residues 439–451; SEQ ID NO:OL, residues 453–459; SEQ ID NO:01, residues 466–478; SEQ ID NO:01, residues 485–499; SEQ ID NO:01, residues 513–523; SEQ ID NO:01, residues 545–550; SEQ ID NO:01, residues 573–584; SEQ ID NO:01, residues 528–537; SEQ ID NO:01, residues 40–45; SEQ ID NO:01, residues 51–65; SEQ ID NO:01, residues 68–75; SEQ ID NO:01, residues 97–107; SEQ ID NO:01, residues 109–116 and SEQ ID NO:01, residues 117–123.

4. The polypeptide of claim 1 comprising an amino acid sequence selected from the group consisting of: SEQ ID NO:02, residues 265–270; SEQ ID NO:02, residues 272–280; SEQ ID NO:02, residues 284–291; SEQ ID NO:02, residues 296–319; SEQ ID NO:02, residues 328–344; SEQ ID NO:02, residues 349–356; SEQ ID NO:02, residues 361–377; SEQ ID NO:02, residues 384–392; SEQ ID NO:02, residues 394–399; SEQ ID NO:02, residues 403–410; SEQ ID NO:02, residues 415–427; SEQ ID NO:02, residues 429–435; SEQ ID NO:02, residues 442–454; SEQ ID NO:02, residues 461–475; SEQ ID NO:02, residues 489–499; SEQ ID NO:02, residues 521–526; SEQ ID NO:02, residues 549–560; SEQ ID NO:02, residues 504–513; SEQ ID NO:02, residues 27–30; SEQ ID NO:02, residues 38–52; SEQ ID NO:02, residues 55–62; SEQ ID NO:02, residues 80–87 and SEQ ID NO:02, residues 88–94.

5. The polypeptide of claim 1 comprising an amino acid sequence selected from the group consisting of: SEQ ID NO:01, residues 289–294; SEQ ID NO:02, residues 265–270; SEQ ID NO:01, residues 296–304; SEQ ID NO:02, residues 272–280; SEQ ID NO:01, residues 308–315; SEQ ID NO:02, residues 284–291; SEQ ID NO:01, residues 320–338; SEQ ID NO:02, residues 296–319; SEQ ID NO:01, residues 345–350; SEQ ID NO:01, residues 352–368; SEQ ID NO:02, residues 328–344; SEQ ID NO:01, residues 373–380; SEQ ID NO:02, residues 349–356; SEQ ID NO:01, residues 385–401; SEQ ID NO:02, residues 361–377; SEQ ID NO:01, residues 408–416; SEQ ID NO:02, residues 384–392; SEQ ID NO:01, residues 418–423; SEQ ID NO:02, residues 394–399; SEQ ID NO:01, residues 427–434; SEQ ID NO:02, residues 403–410; SEQ ID NO:01, residues 439–451 and SEQ ID NO:02, residues 415–427.

6. The polypeptide of claim 1 comprising an amino acid sequence selected from the group consisting of: SEQ ID NO:01, residues 453–459; SEQ ID NO:02, residues 429–435; SEQ ID NO:01, residues 466–478; SEQ ID NO:02, residues 442–454; SEQ ID NO:01, residues 485–499; SEQ ID NO:02, residues 461–475; SEQ ID NO:01, residues 513–523; SEQ ID NO:02, residues 489–499; SEQ ID NO:01, residues 545–550; SEQ ID NO:02, residues 521–526; SEQ ID NO:01, residues 573–584; SEQ ID NO:02, residues 549–560; SEQ ID NO:01, residues 528–537 and SEQ ID NO:02, residues 504–513.

7. The polypeptide of claim 1 comprising an amino acid sequence selected from the group consisting of: SEQ ID NO:01, residues 40–45; SEQ ID NO:02, residues 27–30; SEQ ID NO:01, residues 51–65; SEQ ID NO:02, residues 38–52; SEQ ID NO:01, residues 68–75; SEQ ID NO:02, residues 55–62; SEQ ID NO:01, residues 97–107; SEQ ID NO:01, residues 109–116; SEQ ID NO:02, residues 80–87; SEQ ID NO:01, residues 117–123 and SEQ ID NO:02, residues 88–94.

8. The polypeptide of claim 1 comprising a chicken netrin-1.

9. The polypeptide of claim 1 comprising a chicken netrin-2.

10. An isolated polypeptide comprising a drosophila netrin-a (SEQ ID NO:4) or portion thereof which modulates axon outgrowth or guidance or elicits a drosophila netrin-a—specific antibody.

11. The polypeptide of claim 10 comprising a drosophila netrin-a (SEQ ID NO:4).

12. An isolated polypeptide comprising a mouse netrin-1 (SEQ ID NO:3) or portion thereof which modulates axon outgrowth or guidance or elicits a mouse netrin-1—specific antibody.

13. The polypeptide of claim 12 comprising a mouse netrin-1 (SEQ ID NO:3).

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:

(A) LENGTH: 605 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:1:

```
Met Pro Arg Arg Gly Ala Glu Gly Pro Leu Ala Leu Leu Ala Ala
1               5                   10                  15

Ala Trp Leu Ala Gln Pro Leu Arg Gly Gly Tyr Pro Xaa Leu Asn Met
            20                  25                  30

Phe Ala Val Gln Thr Xaa Ala Asp Pro Cys Tyr Asp Glu His Gly Leu
            35                  40                  45

Pro Xaa Arg Cys Ile Pro Asp Phe Val Asn Ser Ala Phe Gly Lys Glu
    50                  55                  60

Val Lys Val Ser Ser Thr Cys Gly Lys Pro Pro Ser Arg Tyr Cys Val
65                  70                  75                  80

Val Thr Glu Lys Gly Glu Glu Gln Val Arg Ser Cys His Leu Cys Asn
            85                  90                  95

Ala Ser Asp Pro Lys Arg Ala His Pro Pro Ser Phe Leu Thr Asp Leu
            100                 105                 110

Asn Asn Pro His Asn Leu Thr Cys Trp Gln Ser Asp Ser Tyr Val Gln
            115                 120                 125

Tyr Pro His Asn Val Thr Leu Thr Leu Ser Leu Gly Lys Lys Phe Glu
    130                 135                 140

Val Thr Tyr Val Ser Leu Gln Phe Cys Ser Pro Arg Pro Glu Ser Met
145                 150                 155                 160

Ala Ile Tyr Lys Ser Met Asp Tyr Gly Lys Thr Trp Val Pro Phe Gln
            165                 170                 175

Phe Tyr Ser Thr Gln Cys Arg Lys Met Tyr Asn Lys Pro Ser Arg Ala
            180                 185                 190

Ala Ile Thr Lys Gln Asn Glu Gln Glu Ala Ile Cys Thr Asp Ser His
            195                 200                 205

Thr Asp Val Arg Pro Leu Ser Gly Gly Leu Ile Ala Phe Ser Thr Leu
    210                 215                 220

Asp Gly Arg Pro Thr Ala His Asp Phe Asp Asn Ser Pro Val Leu Gln
225                 230                 235                 240

Asp Trp Val Thr Ala Thr Asp Ile Lys Val Thr Phe Ser Arg Leu His
            245                 250                 255

Thr Phe Gly Asp Glu Asn Glu Asp Asp Ser Glu Leu Ala Arg Asp Ser
            260                 265                 270

Tyr Phe Tyr Ala Val Ser Asp Leu Gln Val Gly Gly Arg Cys Lys Cys
    275                 280                 285

Asn Gly His Ala Ser Arg Cys Val Arg Asp Arg Asp Asp Asn Leu Val
    290                 295                 300

Cys Asp Cys Lys His Asn Thr Ala Gly Pro Glu Cys Asp Arg Cys Lys
305                 310                 315                 320

Pro Phe His Tyr Asp Arg Pro Trp Gln Arg Ala Thr Ala Arg Glu Ala
            325                 330                 335

Asn Glu Cys Val Ala Cys Asn Cys Asn Leu His Ala Arg Arg Cys Arg
            340                 345                 350

Phe Asn Met Glu Leu Tyr Lys Leu Ser Gly Arg Lys Ser Gly Gly Val
            355                 360                 365

Cys Leu Asn Cys Arg His Asn Thr Ala Gly Arg His Cys His Tyr Cys
```

-continued

```
                370                 375                 380
Lys Glu Gly Phe Tyr Arg Asp Leu Ser Lys Pro Ile Ser His Arg Lys
385                 390                 395                 400

Ala Cys Lys Glu Cys Asp Cys His Pro Val Gly Ala Ala Gly Gln Thr
                405                 410                 415

Cys Asn Gln Thr Thr Gly Gln Cys Pro Cys Lys Asp Gly Val Thr Gly
                420                 425                 430

Ile Thr Cys Asn Arg Cys Ala Lys Gly Tyr Gln Gln Ser Arg Ser Pro
                435                 440                 445

Ile Ala Pro Cys Ile Lys Ile Pro Ala Ala Pro Pro Thr Ala Ala
450                 455                 460

Ser Ser Thr Glu Glu Pro Ala Asp Cys Asp Ser Tyr Cys Lys Ala Ser
465                 470                 475                 480

Lys Gly Lys Leu Lys Ile Asn Met Lys Lys Tyr Cys Lys Lys Asp Tyr
                485                 490                 495

Ala Val Gln Ile His Ile Leu Lys Ala Glu Lys Asn Ala Asp Trp Trp
                500                 505                 510

Lys Phe Thr Val Asn Ile Ile Ser Val Tyr Lys Gln Gly Ser Asn Arg
                515                 520                 525

Leu Arg Arg Gly Asp Gln Thr Leu Trp Val His Ala Lys Asp Ile Ala
                530                 535                 540

Cys Lys Cys Pro Lys Val Lys Pro Met Lys Lys Tyr Leu Leu Leu Gly
545                 550                 555                 560

Ser Thr Glu Asp Ser Pro Asp Gln Ser Gly Ile Ile Ala Asp Lys Ser
                565                 570                 575

Ser Leu Val Ile Gln Trp Arg Asp Thr Trp Ala Arg Arg Leu Arg Lys
                580                 585                 590

Phe Gln Gln Arg Glu Lys Lys Gly Lys Cys Arg Lys Ala
                595                 600                 605

(2) INFORMATION FOR SEQ ID NO:2:

(i) SEQUENCE CHARACTERISTICS:
        (A) LENGTH: 581 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Leu Arg Leu Leu Leu Thr Thr Ser Val Leu Arg Leu Ala Arg Ala Ala
1               5                   10                  15

Asn Pro Phe Val Ala Gln Gln Thr Pro Pro Asp Pro Cys Tyr Asp Glu
                20                  25                  30

Ser Gly Ala Pro Pro Arg Cys Ile Pro Glu Phe Val Asn Ala Ala Phe
                35                  40                  45

Gly Lys Glu Val Gln Ala Ser Ser Thr Cys Gly Lys Pro Pro Thr Arg
                50                  55                  60

His Cys Asp Ala Ser Asp Pro Arg Arg Ala His Pro Pro Ala Tyr Leu
65                  70                  75                  80

Thr Asp Leu Asn Thr Ala Ala Asn Met Thr Cys Trp Arg Ser Glu Thr
                85                  90                  95

Leu His His Leu Pro His Asn Val Thr Leu Thr Leu Ser Leu Gly Lys
                100                 105                 110

Lys Phe Glu Val Val Tyr Val Ser Leu Gln Phe Cys Ser Pro Arg Pro
```

-continued

```
            115                 120                 125
Glu Ser Thr Ala Ile Phe Lys Ser Met Asp Tyr Gly Lys Thr Trp Val
    130                 135                 140

Pro Tyr Gln Tyr Tyr Ser Ser Gln Cys Arg Lys Ile Tyr Gly Lys Pro
145                 150                 155                 160

Ser Lys Ala Thr Val Thr Lys Gln Asn Glu Gln Glu Ala Leu Cys Thr
                165                 170                 175

Asp Gly Leu Thr Asp Leu Tyr Pro Leu Thr Gly Gly Leu Ile Ala Phe
            180                 185                 190

Ser Thr Leu Asp Gly Arg Pro Ser Ala Gln Asp Phe Asp Ser Ser Pro
        195                 200                 205

Val Leu Gln Asp Trp Val Thr Ala Thr Asp Ile Arg Val Val Phe Ser
210                 215                 220

Arg Pro His Leu Phe Arg Glu Leu Gly Gly Arg Glu Ala Gly Glu Glu
225                 230                 235                 240

Asp Gly Gly Ala Gly Ala Thr Pro Tyr Tyr Tyr Ser Val Gly Glu Leu
                245                 250                 255

Gln Val Gly Gly Arg Cys Lys Cys Asn Gly His Ala Ser Arg Cys Val
            260                 265                 270

Lys Asp Lys Glu Gln Lys Leu Val Cys Asp Cys Lys His Asn Thr Glu
        275                 280                 285

Gly Pro Glu Cys Asp Arg Cys Lys Pro Phe His Tyr Asp Arg Pro Trp
    290                 295                 300

Gln Arg Ala Ser Ala Arg Glu Ala Asn Glu Cys Leu Ala Cys Asn Cys
305                 310                 315                 320

Asn Leu His Ala Arg Arg Cys Arg Phe Asn Met Glu Leu Tyr Lys Leu
                325                 330                 335

Ser Gly Arg Lys Ser Gly Gly Val Cys Leu Asn Cys Arg His Asn Thr
            340                 345                 350

Ala Gly Arg His Cys His Tyr Cys Lys Glu Gly Phe Tyr Arg Asp Leu
        355                 360                 365

Ser Lys Ser Ile Thr Asp Arg Lys Ala Cys Lys Ala Cys Asp Cys His
    370                 375                 380

Pro Val Gly Ala Ala Gly Lys Thr Cys Asn Gln Thr Thr Gly Gln Cys
385                 390                 395                 400

Pro Cys Lys Asp Gly Val Thr Gly Leu Thr Cys Asn Arg Cys Ala Lys
                405                 410                 415

Gly Phe Gln Gln Ser Arg Ser Pro Val Ala Pro Cys Ile Lys Ile Pro
            420                 425                 430

Ala Ile Asn Pro Thr Ser Leu Val Thr Ser Thr Glu Ala Pro Ala Asp
        435                 440                 445

Cys Asp Ser Tyr Cys Lys Pro Ala Lys Gly Asn Tyr Lys Ile Asn Met
    450                 455                 460

Lys Lys Tyr Cys Lys Lys Asp Tyr Val Val Gln Val Asn Ile Leu Glu
465                 470                 475                 480

Met Glu Thr Val Ala Asn Trp Ala Lys Phe Thr Ile Asn Ile Leu Ser
                485                 490                 495

Val Tyr Lys Cys Arg Asp Glu Arg Val Lys Arg Gly Asp Asn Phe Leu
            500                 505                 510

Trp Ile His Leu Lys Asp Leu Ser Cys Lys Cys Pro Lys Ile Gln Ile
        515                 520                 525

Ser Lys Lys Tyr Leu Val Met Gly Ile Ser Glu Asn Ser Thr Asp Arg
    530                 535                 540
```

```
Pro Gly Leu Met Ala Asp Lys Asn Ser Leu Val Ile Gln Trp Arg Asp
545                 550                 555                 560

Ala Trp Thr Arg Arg Leu Arg Lys Leu Gln Arg Arg Glu Lys Lys Gly
                565                 570                 575

Lys Cys Val Lys Pro
                580

(2) INFORMATION FOR SEQ ID NO:3:

(i) SEQUENCE CHARACTERISTICS:
        (A) LENGTH: 529 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Tyr Cys Val Val Ser Glu Arg Gly Glu Arg Val Arg Ser Cys His
1               5                   10                  15

Leu Cys Asn Ser Ser Asp Pro Lys Lys Ala His Pro Pro Ala Phe Leu
                20                  25                  30

Thr Asp Leu Asn Asn Pro His Asn Leu Thr Cys Trp Gln Ser Glu Asn
                35                  40                  45

Tyr Leu Gln Phe Pro His Asn Val Thr Leu Thr Leu Ser Leu Gly Lys
            50                  55                  60

Lys Phe Glu Val Thr Tyr Val Ser Leu Gln Phe Cys Ser Pro Arg Pro
65                  70                  75                  80

Glu Ser Met Ala Ile Tyr Lys Ser Met Asp Tyr Gly Arg Thr Trp Val
                85                  90                  95

Pro Phe Gln Phe Tyr Ser Thr Gln Cys Arg Lys Met Tyr Asn Arg Pro
                100                 105                 110

His Arg Ala Pro Ile Thr Lys Gln Asn Glu Gln Glu Ala Val Cys Thr
                115                 120                 125

Asp Ser His Thr Asp Met Arg Pro Leu Ser Gly Gly Leu Ile Ala Phe
                130                 135                 140

Ser Thr Leu Asp Gly Arg Pro Ser Ala His Asp Phe Asp Asn Ser Pro
145                 150                 155                 160

Val Leu Gln Asp Trp Val Thr Ala Thr Asp Ile Arg Val Ala Phe Ser
                165                 170                 175

Arg Leu His Thr Phe Gly Asp Glu Asn Glu Asp Asp Ser Glu Leu Ala
                180                 185                 190

Arg Asp Ser Tyr Tyr Tyr Ala Val Ser Asp Leu Gln Val Gly Gly Arg
                195                 200                 205

Cys Lys Cys Asn Gly His Ala Ala Arg Cys Val Arg Asp Arg Asp Asp
                210                 215                 220

Ser Leu Val Cys Asp Cys Lys His Asn Thr Ala Gly Pro Glu Cys Asp
225                 230                 235                 240

Arg Cys Lys Pro Phe His Tyr Asp Arg Pro Trp Gln Arg Ala Thr Ala
                245                 250                 255

Arg Glu Ala Asn Glu Cys Val Ala Cys Asn Cys Asn Leu His Ala Arg
                260                 265                 270

Arg Cys Arg Phe Asn Met Glu Leu Tyr Lys Leu Ser Gly Arg Lys Ser
                275                 280                 285

Gly Gly Val Cys Leu Asn Cys Xaa Xaa Asn Thr Xaa Xaa Arg His Cys
                290                 295                 300
```

```
His Tyr Xaa Xaa Gly Gly Xaa Leu Leu Pro Arg His Gly Lys Pro Ile
305                 310                 315                 320

Thr His Arg Lys Ala Cys Lys Ala Cys Asp Cys His Pro Val Gly Ala
            325                 330                 335

Ala Gly Lys Thr Cys Asn Gln Thr Thr Gly Gln Cys Pro Cys Lys Asp
            340                 345                 350

Gly Val Thr Gly Ile Thr Cys Asn Arg Cys Ala Lys Gly Tyr Gln Gln
            355                 360                 365

Ser Arg Ser Pro Ile Ala Pro Cys Ile Lys Ile Pro Val Arg Arg Pro
370                 375                 380

Thr Ala Ala Ser Xaa Val Glu Glu Xaa Xaa Glu Asp Cys Asp Ser Tyr
385                 390                 395                 400

Cys Lys Ala Ser Lys Gly Lys Leu Lys Met Asn Met Lys Lys Tyr Cys
            405                 410                 415

Arg Lys Asp Tyr Ala Val Gln Ile His Ile Leu Lys Ala Asp Lys Ala
            420                 425                 430

Gly Asp Trp Trp Lys Phe Thr Val Asn Ile Ile Ser Val Tyr Lys Gln
            435                 440                 445

Gly Thr Ser Arg Ile Arg Arg Gly Asp Gln Ser Leu Trp Ile Arg Ser
450                 455                 460

Arg Asp Ile Ala Cys Lys Cys Pro Lys Ile Lys Pro Leu Lys Lys Tyr
465                 470                 475                 480

Leu Leu Leu Gly Asn Ala Xaa Asp Ser Pro Asp Gln Ser Gly Ile Val
            485                 490                 495

Ala Asp Lys Ser Ser Leu Val Ile Gln Trp Arg Asp Thr Trp Ala Arg
            500                 505                 510

Arg Leu Arg Lys Phe Gln Gln Arg Glu Lys Gly Lys Cys Lys Lys
            515                 520                 525

Ala (2) INFORMATION FOR SEQ ID NO:4:

(i) SEQUENCE CHARACTERISTICS:
        (A) LENGTH: 727 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Met Ile Arg Gly Ile Leu Leu Leu Leu Gly Thr Thr Arg Phe Ser
1               5                   10                  15

Pro Ile Gln Cys Ile Phe Asn Asp Val Tyr Phe Lys Met Phe Ser Gln
            20                  25                  30

Gln Ala Pro Pro Glu Asp Pro Cys Tyr Asn Lys Ala His Glu Pro Arg
            35                  40                  45

Ala Cys Ile Pro Asp Phe Val Asn Ala Ala Tyr Asp Ala Pro Val Val
            50                  55                  60

Ala Ser Ser Thr Cys Gly Ser Ser Gly Ala Gln Arg Tyr Cys Glu Tyr
65                  70                  75                  80

Gln Asp His Glu Arg Ser Cys His Thr Cys Asp Met Thr Asp Pro Leu
            85                  90                  95

Arg Ser Phe Pro Ala Arg Ser Leu Thr Asp Leu Asn Asn Ser Asn Asn
            100                 105                 110
```

-continued

```
Val Thr Cys Trp Arg Ser Glu Pro Val Thr Gly Ser Gly Asp Asn Val
        115                 120                 125

Thr Leu Thr Leu Ser Leu Gly Lys Lys Phe Glu Leu Thr Tyr Val Ile
        130                 135                 140

Leu Gln Leu Cys Pro His Ala Pro Arg Pro Asp Ser Met Val Ile Tyr
145                 150                 155                 160

Lys Ser Thr Asp His Gly Leu Ser Trp Gln Pro Phe Gln Phe Ser
                165                 170                 175

Ser Gln Cys Arg Arg Leu Phe Gly Arg Pro Ala Arg Gln Ser Thr Gly
            180                 185                 190

Arg His Asn Glu His Glu Ala Arg Cys Ser Asp Val Thr Arg Pro Leu
        195                 200                 205

Val Ser Arg Ile Ala Phe Ser Thr Leu Glu Gly Arg Pro Ser Ser Arg
    210                 215                 220

Asp Leu Asp Ser Ser Pro Val Leu Gln Asp Trp Val Thr Ala Thr Asp
225                 230                 235                 240

Ile Arg Val Val Phe His Arg Leu Gln Arg Pro Asp Pro Gln Ala Leu
                245                 250                 255

Leu Ser Leu Glu Ala Gly Gly Ala Thr Asp Leu Ala Ser Gly Lys Tyr
            260                 265                 270

Ser Val Pro Leu Ala Asn Gly Pro Ala Gly Asn Asn Ile Glu Ala Asn
        275                 280                 285

Leu Gly Gly Asp Val Ala Thr Ser Gly Ser Gly Leu His Tyr Ala Ile
    290                 295                 300

Ser Asp Phe Ser Val Gly Gly Arg Cys Lys Cys Asn Gly His Ala Ser
305                 310                 315                 320

Lys Cys Ser Thr Asp Ala Ser Gly Gln Leu Asn Cys Glu Cys Ser His
                325                 330                 335

Asn Thr Ala Gly Arg Asp Cys Glu Arg Cys Lys Pro Phe His Phe Asp
            340                 345                 350

Arg Pro Trp Ala Arg Ala Thr Ala Lys Glu Ala Asn Glu Cys Lys Glu
        355                 360                 365

Cys Asn Cys Asn Lys His Ala Arg Gln Cys Arg Phe Asn Met Glu Ile
    370                 375                 380

Phe Arg Leu Ser Gln Gly Val Ser Gly Gly Val Cys Gln Asn Cys Arg
385                 390                 395                 400

His Ser Thr Thr Gly Arg Asn Cys His Gln Cys Lys Glu Gly Phe Tyr
                405                 410                 415

Arg Asp Ala Thr Lys Pro Leu Thr His Arg Lys Val Cys Lys Ala Cys
            420                 425                 430

Asp Cys His Pro Ile Gly Ser Ser Gly Lys Ile Cys Asn Ser Thr Ser
        435                 440                 445

Gly Gln Cys Pro Cys Lys Asp Gly Val Thr Gly Leu Thr Cys Asn Arg
    450                 455                 460

Cys Ala Arg Gly Tyr Gln Gln Ser Arg Ser His Ile Ala Pro Cys Ile
465                 470                 475                 480

Lys Gln Pro Pro Arg Met Ile Asn Met Leu Asp Thr Gln Asn Thr Ala
                485                 490                 495

Pro Glu Pro Asp Ala Pro Glu Ser Ser Pro Gly Ser Gly Asp Arg
            500                 505                 510

Asn Gly Ala Ala Glu Trp Pro Pro Ser Leu Ser Thr Ile Ala Pro Arg
        515                 520                 525

Ala Ala Gly Val Lys Cys Gly Lys Cys Arg Val Ser Thr Lys Arg Leu
```

```
                    530                     535                      540
Asn Leu Asn Lys Phe Cys Lys Arg Asp Tyr Ala Ile Met Ala Lys Val
545                 550                 555                 560

Ile Gly Arg Asp Thr Ser Ser Glu Ala Val Ser Arg Glu Val Gln Arg
                565                 570                 575

Arg Ala Met Asp Pro Asp Val Ala Asp Tyr Glu Met Asp Gln Val Gln
            580                 585                 590

Pro Gly Ser Ala Arg Ser Pro Ile Thr Gly Val Tyr Glu Phe Gln Ala
        595                 600                 605

Ala Asp Tyr Pro Asn Pro Asn Pro Asn Pro Arg Gly Ser Glu Met Glu
    610                 615                 620

Arg Phe Asp Leu Gln Ile Gln Ala Val Phe Lys Arg Thr Arg Pro Gly
625                 630                 635                 640

Glu Ser Ser Gly Ala Gly Asn Val Tyr Gly Met Pro Asn Thr Thr Leu
                645                 650                 655

Lys Arg Gly Pro Met Thr Trp Ile Ile Pro Thr Lys Asp Leu Glu Cys
                660                 665                 670

Arg Cys Pro Arg Ile Arg Val Asn Arg Ser Tyr Leu Ile Leu Gly Arg
            675                 680                 685

Asp Ser Glu Ala Pro Pro Gly Tyr Leu Gly Ile Gly Pro His Ser Ile
    690                 695                 700

Val Ile Glu Trp Lys Glu Asp Trp Tyr Arg Arg Met Lys Arg Phe Gln
705                 710                 715                 720

Arg Arg Ala Arg Thr Cys Ala
                725
```